(12) United States Patent
DeMayo

(10) Patent No.: US 6,582,438 B2
(45) Date of Patent: Jun. 24, 2003

(54) BONE GRAFT INSERTER DEVICE

(75) Inventor: Edward DeMayo, Greenbrae, CA (US)

(73) Assignee: IMP, Inc., Plainville, CT (US)

( * ) Notice: Subject to any disclaimer, the term of this patent is extended or adjusted under 35 U.S.C. 154(b) by 75 days.

(21) Appl. No.: 09/966,207

(22) Filed: Sep. 28, 2001

(65) Prior Publication Data

US 2003/0065333 A1 Apr. 3, 2003

(51) Int. Cl.[7] ............................................... A61B 17/58
(52) U.S. Cl. ........................................... 606/92; 606/94
(58) Field of Search .............................. 606/92, 93, 94, 606/80, 86; 604/187, 191, 218, 226; 222/391, 327

(56) References Cited

U.S. PATENT DOCUMENTS

| | | | | |
|---|---|---|---|---|
| 4,751,921 A | * | 6/1988 | Park ............................ | 606/93 |
| 6,093,170 A | * | 7/2000 | Hsu et al. .................... | 604/110 |
| 6,142,998 A | * | 11/2000 | Smith et al. .................. | 606/86 |
| 6,319,233 B1 | * | 11/2001 | Jansen et al. ................ | 604/192 |
| 6,383,190 B1 | * | 5/2002 | Preissman .................... | 606/94 |
| 6,423,033 B1 | * | 7/2002 | Tsai ............................. | 604/110 |

* cited by examiner

Primary Examiner—Pedro Philogene

(57) ABSTRACT

A surgical tool in the form of a three piece bone graft inserter includes a pair of concentric cylinders having elongated apertures formed in the side walls of the cylinders to allow the interior of one of the cylinders to be loaded with the bone graft material, and a plunger that extends through both cylinders. Rotating one of the cylinders thereby "closes" "the apertures creating a closed cylinder filled with the graft material. The ends of the cylinders are inserted into the bone void and the plunger is advanced forward to move the graft material into the bone cavity.

9 Claims, 3 Drawing Sheets

BONE GRAFT INSERTER DEVICE

BACKGROUND OF THE INVENTION

Various surgical bone insert tools are currently available to insert bone graft material within open fractures and large wounds within bones during orthopedic surgery to induce bone formation in fractures and fusions.

One method for delivering bone graft to a receptor site utilizing a hollow cylindrical cutter and a solid inner cylindrical plunger is found in U.S. Pat. No. 5,152,763 entitled "Method for Grafting Bone".

A more recent method is found in U.S. Pat. No. 6,045,555 entitled "Bone Graft Delivery System and Method". This patent discloses a hollow cylindrical cutter and a solid inner cylindrical plunger. The cutter has a cutting end and a grasping end, with the cutter having a cutting end being tapered to a sharp edge for cutting the bone graft from the donor site.

The use of bone graft insert materials in the form of thick putty-like demineralized bone, such as Grafton, which is a registered trademark of Osteotech Inc. for human bone processed into liquid gels and pastes for use in musculoskeletal surgery, impedes the use of such cylindrical insert tools because of the difficulty involved in loading the gels and pastes into the cylinders.

One purpose of the instant invention, accordingly, is to describe a simple effective means for loading the bone graft insert paste material into a cylindrical insert tool for use in bone graft insert surgery.

SUMMARY OF THE INVENTION

A surgical bone graft outer tool in the form of a three piece bone graft inserter includes a pair of concentric cylinders having elongated apertures formed in the side walls of the cylinders and a plunger. The bone graft material is introduced through the apertures then one of the cylinders is rotated to retain the graft material within the cylinders. The plunger is advanced to force the graft material through the cylinders to within the graft insert site.

DESCRIPTION OF THE PREFERRED EMBODIMENT

Figure 1:
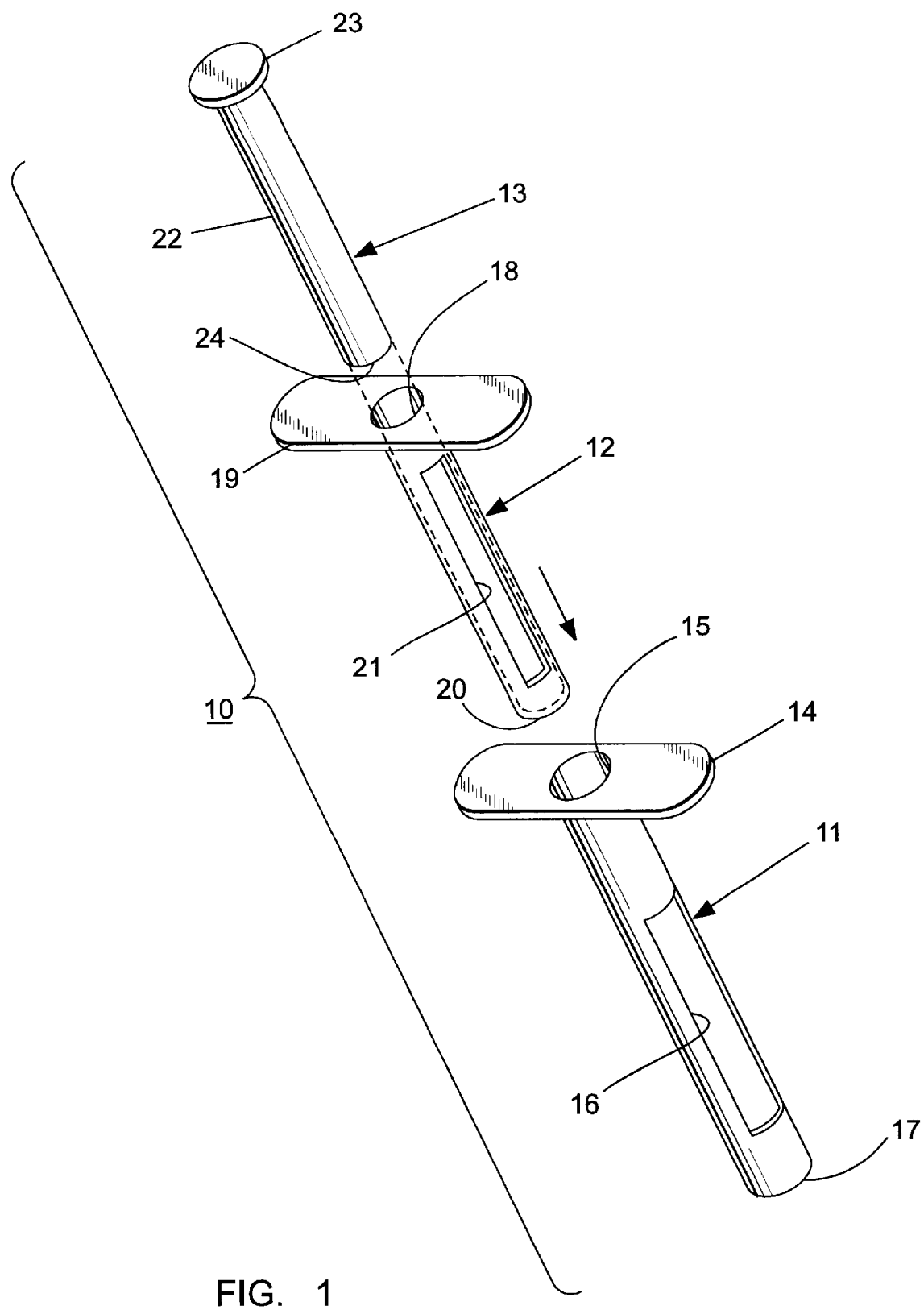
FIG. 1 is a front perspective view of the surgical bone graft outer tool according to the invention, with the components arranged in isometric projection.

The bone graft inserter tool, hereafter "inserter tool" 10 is shown prior to assembly in FIG. 1. The three basic components such as the outer cylinder 11, carrier cylinder 12 and plunger 13 are fabricated from surgical steel for ease in sterilization as well as durability.

The outer cylinder 11 includes a thru-hole 15 extending from the flange 14 at the top end to the tapered opening 17 at the bottom end thereof. In accordance with the teachings of the invention, an elongated aperture 16 extends along the side of the outer cylinder for receiving the bone graft material in the manner to be discussed below in greater detail.

The carrier cylinder 12 also includes a thru-hole 18 extending from the flange 21 at the top end to the planar opening 20 at the bottom end thereof. A similar elongated aperture 21 extends along the side of the carrier cylinder and is co-extensive with the elongated aperture 16 along the outer cylinder 11 when the carrier cylinder 12 is positioned within the outer cylinder 11 is clearance relation.

The plunger 13 is in the form of a solid cylinder 22 that extends from the cap 23 at the top end to the planar end 24 at the bottom thereof. The plunger is positioned within the concentric outer and carrier cylinders after the bone graft material has been inserted therein.

Figure 2:
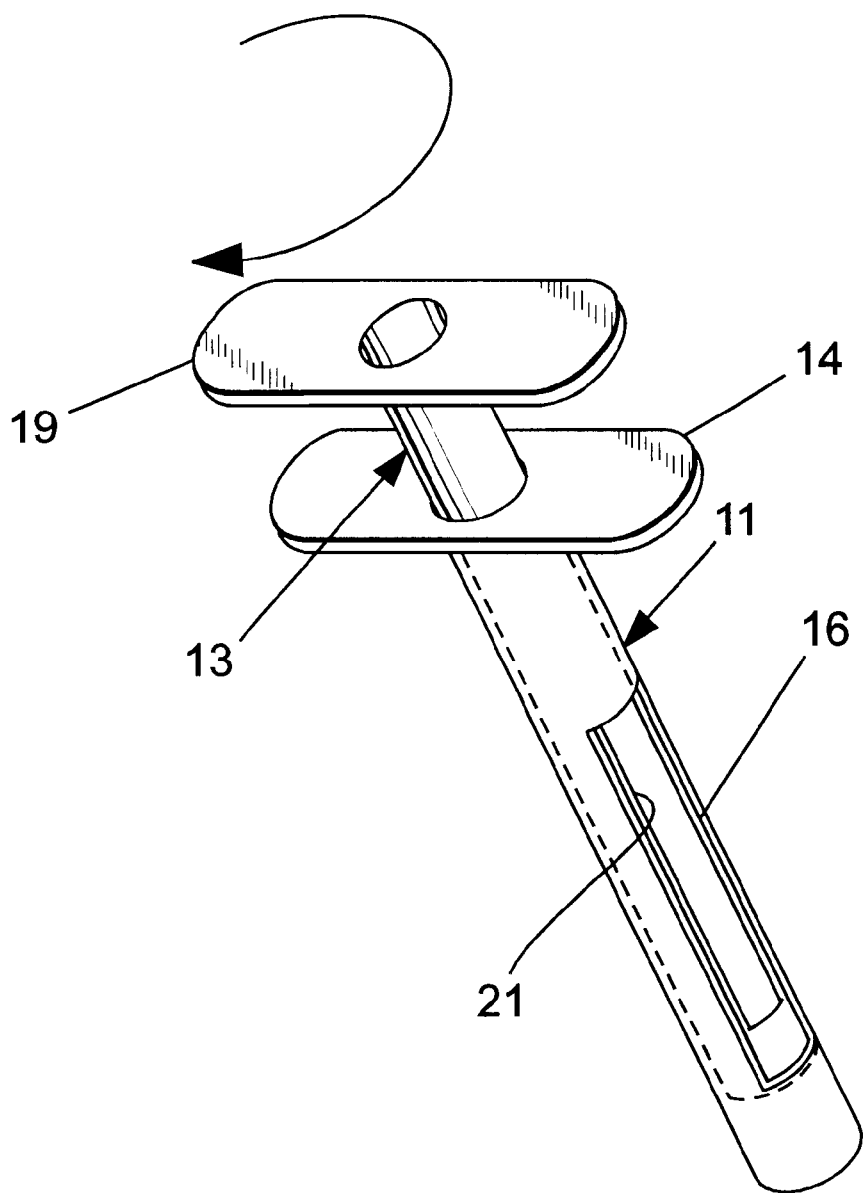
FIG. 2 is a front perspective view of the assembled bone graft outer tool of FIG. 1 with the cylinder apertures depicted in the "open" position.

As best seen by referring now to FIG. 2, the inserter tool 10 is positioned for reception of the bone graft material with the carrier cylinder 12 within the outer cylinder 11. The plunger 13 is omitted for purposes of clarity. The elongated side aperture 16 on the outer cylinder 11 remains in a fixed open position with the elongated side aperture 21 on the carrier cylinder 12 arranged in the open position for receiving the bone graft material within the carrier cylinder. It is noted that the flange 19 on the carrier cylinder 12 is aligned with the flange 14 on the outer cylinder 11. When the carrier cylinder 13 is filled with the bone graft material 25, (FIG. 3) the flange 19 on the carrier cylinder is rotated in the indicated direction to move the elongated side aperture 21 on the carrier cylinder 12 out of alignment with the elongated side aperture 16 on the outer cylinder 11.

Figure 3:
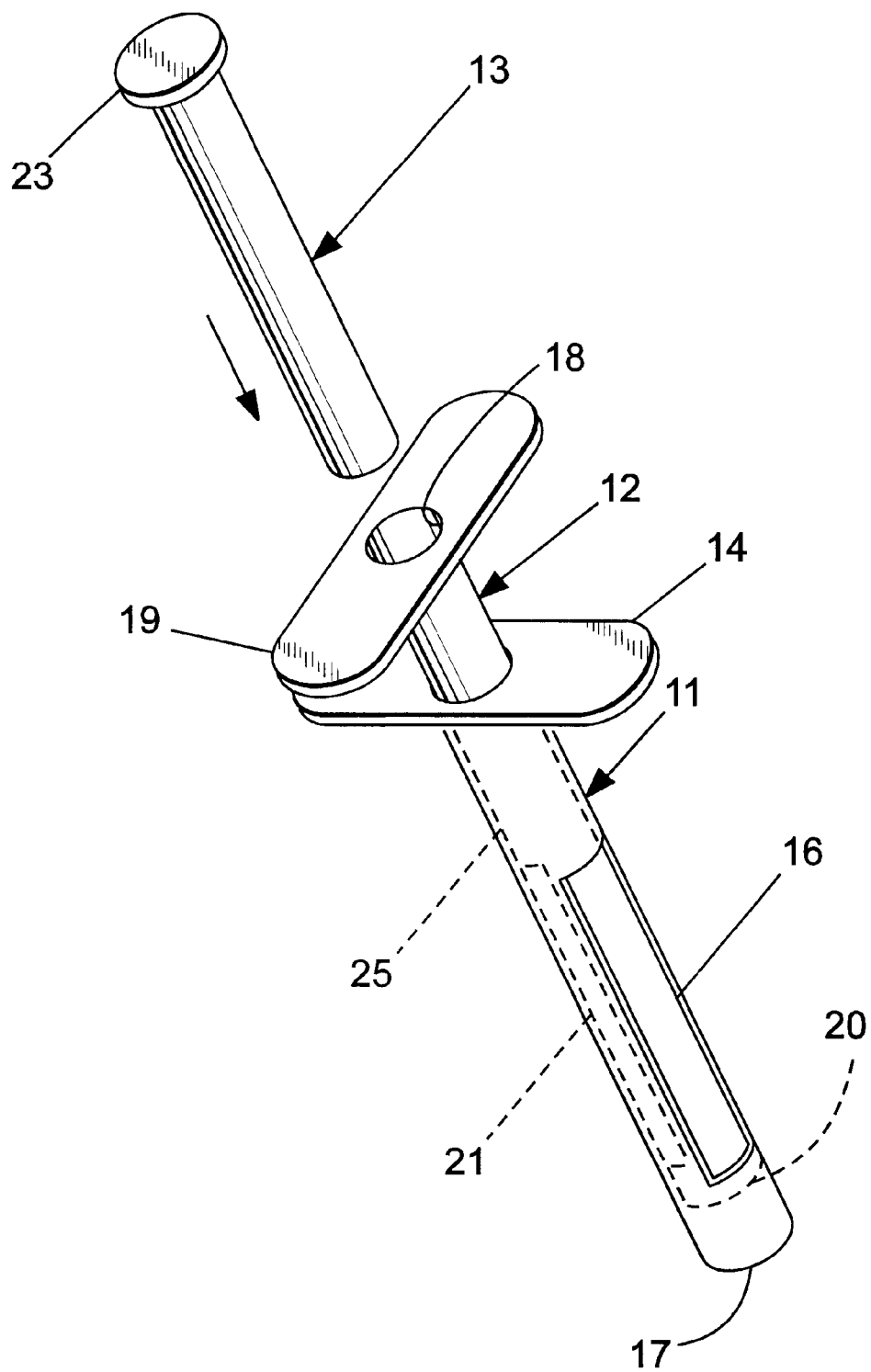
FIG. 3 is a front perspective view of the assembled bone graft outer tool of FIG. 1 with the cylinder apertures depicted in the "closed" position.

In the closed position, as now shown in FIG. 3, the elongated side aperture 21 on the carrier cylinder 12 out of alignment with the elongated side aperture 16 on the outer cylinder 11 such that the bone graft material 25 is now captured within the carrier cylinder 13. The plunger 13 is next inserted within the central aperture 18 of the carrier cylinder 13 complete the assembly and to allow the dispensing of the bone graft material 25 out through the bottom openings 17, 20 of the outer cylinder 11 and the carrier cylinder 12 by digital pressure applied to the plunger cap 23.

What the inserter tool 10 filled with the bone graft material, the bottom openings 17, 20 are positioned slightly within the opening in the bone cavity and the plunger is advanced to expel the bone graft material into the bone cavity.

A surgical bone graft material dispensing tool has herein been described having means for receiving the bone graft material without contamination and without the requirement of additional tools and the like.

What is now claimed is:

1. A bone graft material dispenser comprising:
   an outer cylinder having a top opening at one end and a bottom opening at an opposite end, said outer cylinder further including an elongated aperture on a side thereof intermediate said top and bottom openings;
   a carrier cylinder having a top opening at one end and a bottom opening at an opposite end, said carrier cylinder further including an elongated aperture on a side thereof intermediate said top and bottom openings;
   said carrier cylinder being concentrically arranged within said outer cylinder, whereby said elongated aperture on said carrier cylinder aligns with said elongated aperture on said outer cylinder for allowing said carrier cylinder to receive bone graft material.

2. The bone graft material dispenser of claim 1 further including means for dispensing said bone graft material out of said outer cylinder bottom opening and said carrier cylinder bottom opening.

3. The bone graft material dispenser of claim 2 wherein said outer cylinder includes a flange extending from said outer cylinder top open end.

4. The bone graft material dispenser of claim 2 wherein said carrier cylinder includes a flange extending from said carrier cylinder top open end.

5. The bone graft material dispenser of claim 1 wherein said carrier cylinder is movable arranged within said outer cylinder whereby rotation of said carrier cylinder moves said elongated aperture on said carrier cylinder out of alignment with said elongated aperture on said outer cylinder.

6. The bone graft material dispenser of claim 2 wherein said means for dispensing said bone graft material comprises a plunger.

7. A method for loading bone graft material within a surgical bone graft insertion tool comprising the steps of:

providing an outer cylinder having a concentric opening extending to a proximal top end to a distal bottom end thereof and an elongated opening in a side of said outer cylinder intermediate said top end and said bottom end;

inserting an inner cylinder within said outer cylinder, said inner cylinder having a concentric opening extending from a top end to a bottom end thereof and an elongated opening in a side of said outer cylinder intermediate said top end and said bottom end;

aligning said elongated opening on said inner cylinder with said elongated opening on said outer cylinder to provide a passage for bone graft material to within said inner cylinder; and rotating said inner cylinder to move said elongated opening on said inner cylinder out of alignment with said elongated opening on said outer cylinder to retain said bone graft material within said inner cylinder.

8. A method for loading bone graft material within a surgical bone graft insertion tool comprising the steps of:

providing an outer cylinder having a concentric opening extending from a top end to a bottom end thereof and an elongated opening in a side of said outer cylinder intermediate said top end and said bottom end;

inserting an inner cylinder within said outer cylinder, said inner cylinder having a concentric opening extending from a top end to a bottom end thereof and an elongated opening in a side of said outer cylinder intermediate said top end and said bottom end;

aligning said elongated opening on said inner cylinder with said elongated opening on said outer cylinder to provide a passage for bone graft material to within said inner cylinder; and rotating said outer cylinder to move said elongated opening on said outer cylinder out of alignment with said elongated opening on said inner cylinder to retain said bone graft material within said inner cylinder.

9. The method of claim 7 including the step of:

inserting a dispenser cylinder within said top end of said inner cylinder; and moving an end of said dispenser cylinder against said bone graft material to expel said bone graft material out of said bottom end of said inner cylinder.

* * * * *